United States Patent [19]

Hosztafi et al.

[11] Patent Number: 4,647,694
[45] Date of Patent: Mar. 3, 1987

[54] PROCESS FOR THE PREPARATION OF DI-β-ARYL AMINO ACIDS

[75] Inventors: Sándor Hosztafi, Monostorpályi; Tibor Timár; Zoltán Salamon, Ilona Fabian nee Orbán; Julianna Nagy nee Vajda of Tiszavasvári, all of Hungary

[73] Assignee: Alkaloida Vegyeszeti Gyar, Tiszavasvari, Hungary

[21] Appl. No.: 710,838

[22] Filed: Mar. 12, 1985

[30] Foreign Application Priority Data

Mar. 12, 1984 [HU] Hungary ........................ 981/84

[51] Int. Cl.$^4$ ........................................... C07C 99/08
[52] U.S. Cl. ................................. 562/443; 548/308; 562/437; 562/444; 562/445
[58] Field of Search ............... 562/442, 443, 444, 445, 562/437, 575; 548/308

[56] References Cited

U.S. PATENT DOCUMENTS

| | | | |
|---|---|---|---|
| 2,861,079 | 11/1958 | Britton et al. | 548/308 |
| 3,190,914 | 6/1965 | Williams | 562/575 |
| 3,215,736 | 11/1965 | Guinot | 562/575 |
| 3,475,489 | 10/1969 | de Graaf et al. | 562/575 |
| 3,637,804 | 1/1972 | Hegedus et al. | 548/308 |
| 3,790,599 | 2/1974 | Nundel | 562/443 |
| 3,946,033 | 3/1976 | Iwata et al. | 548/308 |
| 4,175,198 | 11/1979 | Gaudette | 548/308 |

FOREIGN PATENT DOCUMENTS

| | | | |
|---|---|---|---|
| 37480 | 3/1981 | European Pat. Off. | 548/308 |
| 54-106470 | 8/1979 | Japan | 548/308 |
| 54-106469 | 8/1979 | Japan | 548/308 |
| 54-128572 | 10/1979 | Japan | 548/308 |
| 54-138559 | 10/1979 | Japan | 548/308 |
| 991644 | 5/1965 | United Kingdom | 548/308 |

OTHER PUBLICATIONS

Kochkanyan et al, Chem. Abst., vol. 88, #152,500z, (1978).
Lippich, Berichte, 41, 2953-2983, (1908).

Primary Examiner—James H. Reamer
Attorney, Agent, or Firm—Karl F. Ross; Herbert Dubno

[57] ABSTRACT

The invention relates to a process for the preparation of DL-β-aryl-amino acids of the general Formula

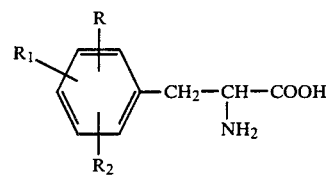

wherein
R, $R_1$ and $R_2$ stand for hydrogen, halogen, $C_{1-6}$ alkyl, $C_{1-6}$ alkoxy, nitro or $C_{1-4}$ dialkylamino; whereby
in the case of monosubstituted derivatives R and $R_1$ are hydrogen and $R_2$ has the same meaning as stated above and can be attached to position 2, 3 or 4 related to the methylene group;
in the case of disubstituted derivatives R is hydrogen and $R_1$ and $R_2$ have the same meaning as stated above and are attached to positions 2,3; 2,4; 2,5; 2,6; 3,4 or 3,5 related to the methylene group;
in the case of trisubstituted derivatives R, $R_1$ and $R_2$ have the same meaning as stated above and are attached to positions 2,3,4; 2,3,5; 2,3,6; 3,4,5 or 3,4,6 related to the methylene group.

11 Claims, No Drawings

PROCESS FOR THE PREPARATION OF Dl-β-ARYL AMINO ACIDS

FIELD OF THE INVENTION

This invention relates to a new and improved process for the preparation of DL-β-aryl-amino acids of the Formula

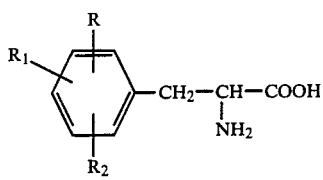

V from hydantoin.

BACKGROUND OF THE INVENTION

Several industrial scale processes are known for the preparation of hydantoin of the Formula

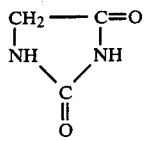

I

According to E. Ware [Chem.Rev. 46, 403 (1950)] glycine ethyl ester or glycine nitrile is reacted with potassium cyanate, or glycine nitrile or lactic acid nitrile is treated with ammonium carbonate and the hydantoinic acid intermediate thus obtained is converted into hydantoin by acidic cyclization. Hydantoin is also formed by melting glycine and urea, while the reaction can be accomplished with nitro urea in aqueous solution too. The reaction of various amino acids (i.e. glycine) with urea in aqueous solution in the presence of barium hydroxide was studied. The first step of the synthesis of β-aryl amino acids starting from hydantoin is the condensation reaction of the corresponding aromatic aldehyde of the Formula

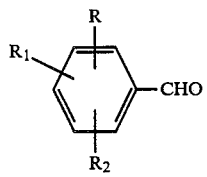

II with hydantoin of the Formula I to yield the corresponding 5-arylidene hydantoin of the Formula

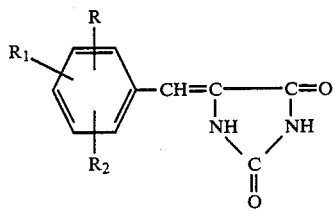

III

As the condensing agent in acetic acid sodium acetate may be used or in pyridine as solvent, secondary amines (e.g. diethyl amine, piperidine) can be used [E. Ware: Chem. Rev. 46, 403 (1950); G. Billek: Monatsch. 92, 352 (1961)].

The condensation reaction can also be carried out in aqueous medium in the presence of ethanol amine (cholamine)—see U.S. Pat. No. 2,861,079.

In the next step of the synthesis the 5-arylidene-hydantoin of the Formula III is reduced into the corresponding 5-aryl-methyl-hydantoin of the Formula

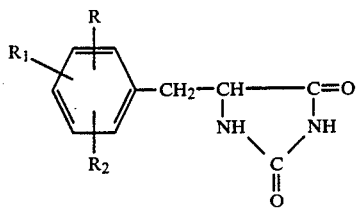

IV

The reduction can be carried out with hydrogen iodide/red phosphorous, or hydrogen iodide in glacial acetic acid or by catalytic hydrogenation [E. Ware: Chem.Rev. 46, 403 (1950)]. As the catalyst palladium/-charcoal or platinum oxide in alcoholic medium (methanol or ethanol) can be used [M. L. Sethi et al.: J.Pharm.-Sci. 62, 1802 (1973)] or Raney-nickel can be applied in methanolic solution under a pressure of 720 atm. at 85° C. [U.S. Pat. No. 2,479,065] or in aqueous medium [H. P. Ward: J.Am.Chem.Soc. 74, 4212 (1952)].

The 5-aryl-methyl-hydantoin of the Formula IV can be converted by hydrolysis into the corresponding DL-β-aryl amino acid of the Formula V. The hydantoin ring can be hydrolysed in acidic medium, e.g. by means of 60% sulfuric acid [L. H. Goodson et al.: J.Org.Chem. 25, 1920 (1960)] or with the aid of 57% hydrogen iodide/red phosphorous [H. L. Wheelerm, C. Hoffman: Am.Chem.J.: 45, 568 (1911); C.A. 5, 2072].

Alkaline hydrolysis is however generally much favorable. For this purpose barium hydroxide can be used [H. L. Wheeler, C. Hoffman: Am.Chem.J. 45 568 (1911); CA 5 2072; R. Gaudri: Can.J.Research 26B 773 (1948); H. Finkbeiner: J.Org.Chem. 30 3414 (1965)], or sodium hydroxide can be applied [E. Pierson et al: J.Am.Chem.So. 70 1450 (1948); M. Matsui, M. Nishio: Agr.Biol.Chem. (Tokyo) 28 710 (1964); K. Okubo, Y. Izumi: Bull.Chem.Soc.Jap. 43 1541 (1970); M. L. Sethi et al.: J.Pharm.Sci. 62 1802 (1973)] in concentrated aqueous solution. Several 5-substituted hydantoin derivatives can be hydrolyzed in an autoclave at (180° C. for 90 minutes) to yield the corresponding amino acid in a solution of $Na_2MoO_4.2H_2O$ (KOKAI No. 74-116,008).

L-amino acids can be directly formed by enzymatic hydrolysis of the corresponding racemic 5-substituted hydantoins [U.S. Pat. No. 4,016,037; KOKAI Nos. 77-18,837 and 78-34,990; G. Marcel et al: Bull.Soc.-Chim.Fr. 1-2 Pt.2 91(1980)].

The reaction of glycine and urea seems to be the most preferred industrial scale synthesis of hydantoin. The reaction carried out in the melt is unsuitable for industrial scale production because of the low yields and technical problems. It is preferred to carry out the reaction in aqueous medium. When preparing arylidene hydantoines, it is highly preferred to work in an aqueous medium in the presence of ethanol amine. A comparison with the glacial acetic acid/sodium acetate method shows that the yield is higher and the costs are lower.

The saturation of 5-arylidene hydantoins can be carried out most advantageously in the presence of a Raney-nickel because this catalyst is the cheapest and the yields are also higher.

Hydrogenation can be carried out preferably in a diluted sodium hydroxide solution since in this system the solubility conditions are better than in alcohols.

The barium hydroxide hydrolysis method suggested as preferable for the splitting of the hydantion ring has several drawbacks:

a. a part of the starting material remains unreacted and unchanged;

b. on removing the barium ions the solution is acidified with sulfuric acid and a finely distributed barium sulfate precipitate formed causes significant losses-due to adsorption.

Hydrolysis carried out with sodium hydroxide results in certain cases only the corresponding hydantoin acid. Acidic hydrolysis is unsuitable because of the low yields.

DESCRIPTION OF THE INVENTION

According to the process of the present invention hydantoine of the Formula I is prepared with a yield of 70-75% by heating to boiling an aqueous solution of glycine and an excess of urea (without isolating the hydantoin acid intermediate) and subjecting the mixture to acidic cyclization. At the end of the reaction the desired product precipitates in crystalline form and can be directly used in the next step. By evaporating the mother liquor and extracting the crystalline residue with methanol a further amount of the product can be obtained.

The ratio between the glycine and the urea that is preferred in the first step of the new process is a molar ratio of 1:1.8 to 1:5, preferably 1:2.3. The reaction is preferably carried out at the boiling point of the mixture. To facilitate the cyclization reaction to form the hydantoin, sulfuric acid is then added in concentrated form in an amount of 1:0.3 to 1:1, preferably 1:0.5 relative to the glycine.

The hydantoin is formed as a precipitate in crystalline form and the mother liquor that forms above the precipitate may itself then be evaporated and the residue extracted with a 5 to 25-fold, preferably a 10-fold amount of methanol, to recover additional hydantoin.

The aqueous solution of the hydantoin of the Formula I and an equimolar amount of an aromatic aldehyde of the Formula II is heated in the presence of an excess of ethanol amine or morpholine for 4 hours and the corresponding 5-arylidene hydantoin of the Formula III may be isolated after acidification with a yield of 90%. The ethanol amine or morpholine can be recovered by alkalizing the mother liquor and distillation; the recovered amine can be re-introduced into the reaction.

It has been found that the reduction of the 5-arylidene hydantoins of the Formula III can be carried out easily and with good yields in a diluted sodium hydroxide solution, with a Raney nickel catalyst, at room temperature, under atmospheric pressure or a pressure or 3-5 bar.

The 5-aryl methyl hydantoin of the Formula IV thus obtained can be hydrolyzed into the corresponding DL-$\beta$-aryl amino acid of the Formula V in a 20% sodium hydroxide solution with good yields, whereby the corresponding hydantoinic acid is formed but in a negligible amount.

It is preferred to carry out hydrolysis in the presence of cellosolve since this results in an increase of the yield and the cellosolve can be recovered by distillation. The yield can be further increased by accomplishing hydrolysis in an autoclave (at 140° C.), thus the reaction time can also be shortened.

In the Formulae

R, $R_1$ and $R_2$ stand for hydrogen, halogen, $C_{1-6}$ alkyl, $C_{1-6}$ alkoxy, nitro or $C_{1-4}$ dialkylamino; whereby in the case of monosubstituted derivatives R and $R^1$ are hydrogen and $R_2$ has the same meaning as stated above and can be attached in position 2, 3, or 4 relative to the methylene group;

in the case of disubstituted derivatives R is hydrogen and $R_1$ and $R_2$ have the same meaning as stated above and are attached in positions 2,3; 2,4; 2,5; 2,6; 3,4 or 3,5 relative to the methylene group;

in the case of trisubstituted derivatives R, $R_1$ and $R_2$ have the same meaning as stated above and are attached to positions 2,3,4; 2,3,5; 2,3,6; 3,4,5 or 3,4,6 related in the methylene group.

A further advantage of the process of the present invention is that the 5-aryl-methyl hydantoins of the Formula IV are obtained in very high yields and in such a purity that they can be directly converted into the L-amino acids by enzymatic hydrolysis.

SPECIFIC EXAMPLES

Further details of the present invention are to be found in the following examples without limiting the scope of protection to the said examples.

The purity of the compounds disclosed in the examples is checked by physical constants and HPLC methods. The melting points disclosed are non-corrected values. In certain cases the structure of the compounds is confirmed by IR, FT-NMR and MS spectra.

EXAMPLE 1

Hydantoine (I)

75 g (1 mole) of glycine and 140 g (2.3 moles) of urea are dissolved in 120 ml of water and the mixture is heated to boiling for 12 hours under stirring. To the reaction mixture 90 ml of concentrated sulfuric acid are added dropwise under cooling with ice cold water and stirring. The reaction mixture is heated to boiling for an hour and thereafter cooled to 0°-5° C. The hydantoin precipitates in crystalline form. The crystals are filtered off, washed with cold water. A further amount of the product can be obtained by evaporating the mother liquor. Thus 71 g of the desired compound are obtained, yield 70%, mp.: 223°-226° C.

The crude hydantoin thus obtained is sufficiently pure for further reaction. It can be recrystallized from 10 parts of glacial acetic acid, mp.: 220-222° C.

EXAMPLE 2

5-benzylidene-hydantoine (III)

50 g (0.5 mole) of hydantoin, 55 g (52 ml, 0.52 mole) of benzaldehyde and 46 g (45 ml, 0.7 mole of ethanol amine are admixed in 500 ml of water at 70° C. The temperature is raised to 90° C. and the reaction mixture is stirred for 4 hours. The solution is cooled and acidified with concentrated hydrochloric acid (pH 3-4). The mixture is allowed to stand at 10° C. for an hour, the product is filtered off, washed with cold water and dried. Thus 84.5 g of the desired compound are obtained, yield 89%. Mp.: 220°-222° C.

On comparing the product with a standard sample of 5-benzylidene-hydantoin by HPLC the purity proved to be 100%.

EXAMPLE 3

5(2-methoxy-benzylidene)hydantoin (III)

50 g (0.5 mole) of hydantoin, 68.07 1 g (0.5 mole) of salicylaldehyde-methyl-ether and 46 g (0.7 mole) of ethanol amine are admixed in 500 ml of water at 70° C. The reaction mixture is worked up as described in Example 2. Thus 90.6 g of the desired compound are obtained, yield 83%, mp.: 178° C.

EXAMPLE 4

5-(4-methoxy-benzylidene)-hydantoin (III)

50 g (0.5 mole) of hydantoin, 68.07 g (0.5 mole) of 4-methoxy-benzylaldehyde and 46 g (0.7 mole) of ethanol amine are admixed in 500 ml of water at 70° C. The reaction is carried out further as described in Example 2. Thus 92.7 g of the desired compound are obtained, yield 85%. Mp.: 242°-244° C.

EXAMPLE 5

5-(3,4,5-trimethoxy-benzylidene)-hydantoin (III)

50 g (0.5 mole) of hydantoine, 98.1 g (0.5 mole) of 3,4,5-trimethoxy-benzaldehyde and 46 g (0.7 mole) of ethanol amine are admixed with 500 ml of water at 70° C. The reaction is carried out further in accordance with Example 2. Thus 121 g of the desired compound are obtained, yield 87%. Mp.: 266°-268° C.

EXAMPLE 6

5-benzyl-hydantoin (IV)

190 g (1 mole) of 5-benzylidene-hydantoin are dissolved in 2 l of a N sodium hydroxide solution and 95 g of wet Raney-nickel are added. The hydrogen uptake is terminated after about 6-8 hours (the reaction mixture is shaken at atmospheric pressure). The catalyst is filtered off and washed with N sodium hydroxide. The filtrate is acidified to pH 3 with concentrated hydrochloric acid. The precipitated white crystals are filtered off, dried and washed with cold water. Thus 152 g of the desired compound are obtained, yield 80%. Mp.: 187°-189° C.

EXAMPLE 7

5-benzyl-hydantoine (IV)

190 g (1 mole) of 5-benzylidene-hydantoin are dissolved in 2 l of a N sodium hydroxide solution and 40 g of 5% palladium/charcoal catalyst are added. The mixture is hydrogenated at room temperature under atmospheric pressure and under shaking for 4 hours. The reaction mixture is worked up according to Example 6. Thus 150.2 g of the desired compound are obtained, yield 79%. Mp.: 187°-189° C.

EXAMPLE 8

5-(2-methoxy-benzyl)-hydantoin (IV)

218.2 g (1 mole) of 5-(2-methoxy-benzylidene)-hydantoin are dissolved in 2 l of a N sodium hydroxide solution and 70 g of wet Raney-nickel are added. The reaction mixture is worked up according to Example 6. Thus 174 g of the desired compound are obtained, yield 79%. Mp.: 186° C.

EXAMPLE 9

5-(4-methoxy-benzyl)-hydantoin (IV)

218.2 g (1 mole) of 5-(4-methoxy-benzylidene)-hydantoin are dissolved in 2 l of a N sodium hydroxide solution and 50 g of wet Raney-nickel are added. The reaction mixture is worked up according to Example 6. Thus 180.6 g of the desired compound are obtained, yield 82 %. Mp.: 174° C.

EXAMPLE 10

5-(3,4,5-trimethoxy-benzyl)-hydantoine (IV)

278.3 g (1 mole) of 5-(3,4,5-trimethoxy-benzylidene)-hydantoin are dissolved in 2 l of a N sodium hydroxide solution and 40 g of wet Raney-nickel are added. The reaction mixture is worked up according to Example 6. Thus 218.6 g of the desired compound are obtained, yield 78%. Mp.: 180°-181° C.

EXAMPLE 11

DL-phenyl alanine (V)

95.1 g (0.5 mole) of 5-benzyl-hydantoine are dissolved in a solution of 87 g of sodium hydroxide and 400 ml of water, whereupon 300 ml of cellosolve are added. The reaction mixture is heated to boiling for 48 hours, the water and the cellosolve are distilled off in vacuo (30 Hgmm, 80° C.), the solid residue is dissolved in a small amount of water and acidified with concentrated hydrochloric acid (pH 2). The solution is treated with activated charcoal and the pH is adjusted to 6 with a concentrated ammonium hydroxide solution. The mixture is allowed to stand for some hours at 5° C. The precipitated product is filtered off, washed with cold water and cold ethanol. Thus 63.4 g of the desired airdry compound are obtained, yield 77%, mp.: 245°-255° C. Purity: 97.9% according to HPLC.

EXAMPLE 12

DL-phenyl alanine (V)

95.1 g (0.5 mole) of 5-benzyl-hydantoin are heated to boiling in 350 ml of a 20% sodium hydroxide solution for 30 hours. The reaction mixture is clarified with activated charcoal and acidified with concentrated hydrochloric acid (pH 2). The precipitate (hydrantoinic acid) is filtered off and the phenyl alanine is precipitated from the filtrate as described in Example 11. Thus 59.5 g of the dry desired compound are obtained, yield 72%. Purity: 97.5% (according to HPLC).

EXAMPLE 13

DL-2-methoxy-phenyl-alanin (V)

110.1 g (0.5 mole) of 5-(2-methoxy-benzyl)-hydantoin are dissolved in a solution of 90 g sodium hydroxide and 400 ml of water. After the addition of 300 ml of cellosolve the reaction mixture is stirred for 50 hours. The reaction mixture is worked up as described in Example 11. Thus 56.6 g of the desired compound are obtained, yield 58%. Mp.: 205°-208° C.

EXAMPLE 14

DL-4-methoxy-phenyl-alanine (V)

110.1 g (0.5 mole) of 5-(4-methoxy-benzyl)-hydantoin are dissolved in a solution of sodium hydroxide and 400 ml of water. After the addition of 300 ml of cellosolve the reaction mixture is heated to boiling for 50 hours.

The reaction mixture is worked up according to Example 11. Thus 68.3 g of the desired compound are obtained, yield 70%. Mp.: 283°-288° C.

EXAMPLE 15

DL-3,4,5-trimethoxy-phenyl-alanine (V)

140.2 g (0.5 mole) of 5-(3,4,5-trimethoxy-benzyl)-hydantoin are dissolved in a solution of 90 g of sodium hydroxide and 400 ml of water. After the addition of 250 ml of cellosolve the reaction mixture is heated to boiling for 48 hours. The reaction mixture is worked up according to Example 11. Thus 94.1 g of the desired compound are obtained, yield 65% (hydrochloride salt). Mp.: 240°-243° C. (hydrochloride).

What we claim is:

1. A process for the preparation of a compound of the Formula (V)

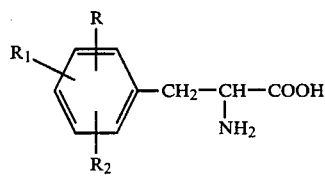

wherein

R, $R_1$, and $R_2$ are each hydrogen, halogen, $C_1$ to $C_6$ alkyl, $C_1$ to $C_6$ alkoxy, nitro, or $C_1$ to $C_4$ dialkylamino whereby, in the case of monosubstituted compounds, R and $R_1$ are each hydrogen, and $R_2$ is halogen, $C_1$ to $C_6$ alkoxy, nitro, or $C_1$ to $C_4$ dialkylamino wherein $R_2$ is bonded to positions 2,3, or 4 relative to the methylene group;

in the case of disubstituted compounds, R is hydrogen and $R_1$ and $R_2$ are each halogen, $C_1$ to $C_6$ alkyl, $C_1$ to $C_6$ alkoxy, nitro, or $C_1$ to $C_4$ dialkylamino wherein $R_1$ and $R_2$ are bonded respectively to positions 2,3; 2,4; 2,5; 2,6; 3,4; or 3,5, relative to the methylene group; and in the case of trisubstituted compounds R,$R_1$ and $R_2$ are each halogen, $C_1$ to $C_6$ alkyl, $C_1$ to $C_6$ alkoxy, nitro, or $C_1$ to $C_4$ dialkylamino whereby R, $R_1$ and $R_2$ are bonded respectively to positions 2,3,4; 2,3,5; 2,3,6; 3,4,5; or 3,4,6 relative to the methylene group, which comprises the steps of:

(a) boiling an aqueous solution of glycine and urea in a molar ratio of 1:1.8 to 1:5 to form hydantoic acid as an intermediate, and directly cyclizing the hydantoic acid intermediate by adding to the solution concentrated sulfuric acid in a molar ratio of 1:0.3 to 1:1 relative to the glycine to form hydantoin of the Formula (I) as a precipitate and a mother liquor:

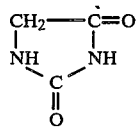

and separating the precipitate of hydantoin from the mother liquor;

(b) condensing the hydantoin formed during step (a) with an aromatic aldehyde of the Formula (II)

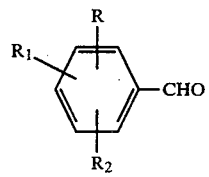

in an aqueous solution in the presence of ethanolamine or morpholine to obtain a 5-arylidene-methyl-hydantoin of the Formula (III)

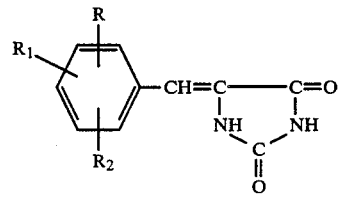

(c) quantitatively reducing the compound of the Formula (III) prepared in step (b) in a diluted alkaline medium in the presence of a Raney nickel or palladium-on-charcoal catalyst, to obtain a 5-aryl-methyl-hydantoin of the Formula (IV)

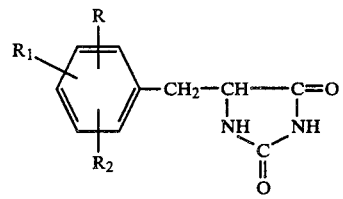

and;

(d) subjecting the compound of the Formula (IV) to alkaline hydrolysis to yield the compound of the Formula (V).

2. The process defined in claim 1 wherein following step (a) the mother liquor is evaporated and a crystalline residue is extracted therefrom with a 5 to 25-fold amount of methanol to yield additional hydantoin.

3. The process according to claim 1, which comprises using hydantoin and the aromatic aldehyde of the Formula II during step 1b in equimolar ratio and using morpholine in a 1-2 molar equivalent amount, and carrying out the reaction of 60°-100° C.

4. The process according to claim 1 which comprises isolating the product after acidifying with concentrated hydrochloric acid, making the mother liquor alkaline and recovering the ethanol amine or morpholine by distillation and re-introducing the same into the reaction.

5. The process according to claim 1 which comprises using the Raney-nickel catalyst during step (c) in a 0.1-1.0-fold amount related to the 5-arylidene hydantoin of the Formula III; or using the palladium on-charcoal catalyst in a 5-30% amount.

6. The process according to claim 1 which comprises carrying out reduction during step (c) in a diluted alkali, preferably a N sodium hydroxide solution, at room temperature, at a pressure of 1-10 bars.

7. The process according to claim 1 which comprises carrying out hydrolysis during step (d) of the 5-arylmethyl-hydantoin of the Formula IV in a 15–40% sodium hydroxide solution, at the boiling point of the reaction mixture, in the presence or absence of cellosolve in an autoclave.

8. The process according to claim 1 which comprises recovering the cellosolve in the hydrolysis step by isolation of the product and by distillation and re-introducing the same into the process.

9. The process according to claim 1 which comprises following step (d) isolating the DL-$\beta$-aryl amino acid of the Formula V at the isoelectric point thereof.

10. The process according to claim 1 wherein the reduction during step (c) of the 5-arylidene-hydantoin of the Formula (III) is carried out in a 1 N sodium hydroxide solution, at room temperature, at a pressure of 1 to 10 bars, using the Raney nickel catalyst in a 0.1 to 1.0 fold amount related to the 5-arylidene-hydantoin of the Formula (III), or using the palladium-on-charcoal catalyst in a 5 to 30% amount.

11. The process according to claim 7 wherein the hydrolysis of the 5-aryl-methyl-hydantoin of the Formula (IV) is carried out in a 20% sodium hydroxide solution.

* * * * *